United States Patent [19]

Sekine et al.

[11] Patent Number: 4,647,431
[45] Date of Patent: Mar. 3, 1987

[54] DEVICE FOR MAINTAINING A CONSTANT TEMPERATURE FOR CHEMICAL ANALYSIS

[75] Inventors: Takasi Sekine; Kenichiro Yazawa; Masao Kitajima, all of Saitama, Japan

[73] Assignee: Fuji Photo Film Co., Ltd., Kanagawa, Japan

[21] Appl. No.: 725,694

[22] Filed: Apr. 22, 1985

Related U.S. Application Data

[63] Continuation of Ser. No. 269,162, Jun. 1, 1981, abandoned.

[30] Foreign Application Priority Data

May 31, 1980 [JP] Japan ............................ 55-75673

[51] Int. Cl.$^4$ ........................................ G01N 35/00
[52] U.S. Cl. ........................................ 422/63; 422/64; 422/65; 422/99; 436/46
[58] Field of Search ........................... 422/63–67, 422/99, 50; 436/46, 44; 435/291; 198/624, 628

[56] References Cited

U.S. PATENT DOCUMENTS

| | | | |
|---|---|---|---|
| 2,915,171 | 12/1959 | Peck | 198/628 |
| 3,429,420 | 2/1969 | Bechtloff et al. | 198/628 |
| 3,533,744 | 10/1970 | Unger | 422/65 |
| 3,675,488 | 7/1972 | Viktora | 422/66 |
| 3,904,369 | 9/1975 | Adler | 422/66 |
| 4,059,405 | 11/1977 | Sodickson et al. | 422/68 |
| 4,067,694 | 1/1978 | Blakely et al. | 422/63 |
| 4,160,646 | 7/1979 | Furutani et al. | 436/44 |
| 4,224,032 | 9/1980 | Glover et al. | 422/65 |
| 4,264,560 | 4/1981 | Natelson | 422/66 |
| 4,303,611 | 12/1981 | Jessop | 422/66 |
| 4,488,810 | 12/1984 | Hatanaka et al. | 422/64 |

*Primary Examiner*—Michael S. Marcus
*Attorney, Agent, or Firm*—Sughrue, Mion, Zinn, Macpeak & Seas

[57] ABSTRACT

A device for maintaining a constant temperature for chemical analysis performed with slides having at least one layer adapted to absorb a substance to be analyzed. The slides are conveyed upon a lower conveying belt which may have projections or recesses formed therein for receiving the slides. The upper portions of the slides are sealed by a sealing guide belt which has a surface disposed parallel to and adjacent the conveying belt with the slides passing therebetween. A heater may be provided within the conveying belt and the guide member provided within the sealing guide belt which may itself perform a heating function.

17 Claims, 6 Drawing Figures

DEVICE FOR MAINTAINING A CONSTANT TEMPERATURE FOR CHEMICAL ANALYSIS

This is a continuation of application Ser. No. 269,162, filed June 1, 1981, abandoned.

BACKGROUND OF THE INVENTION

The present invention relates to a device for maintaining a constant temperature for chemical analysis. In particular, the invention relates to a device for maintaining a constant temperature for chemical analysis wherein a substance to be measured acts on a coloration reagent in a reagent layer of a multilayer chemical analysis film of a chemical analysis slide, the degree of coloration is measured or judged with a high accuracy using an optical system or the like, and the chemical analysis slide can be sealed and maintained at a constant temperature for a desired period of time.

In a test for determining, for example, the concentration of glucose or urea nitrogen in blood, the simplest conventional method is to use a test paper for coloration and to visually compare the degree of coloration of the test paper with a sample color density of a standard concentration of a substance which is to be measured. However, since the determination of the degree of coloration of the test paper depends upon the visual judgement of the human operator, this method is not satisfactory as far as its accuracy is concerned. Modern developments in medicine require a higher accuracy than can be obtained using this method.

There have been proposed various types of chemical analysis slides each having a multilayer chemical analysis film which is composed of at least two layers, specifically, a spreading layer and a reagent layer which is adapted for automatic analysis using an optical system. Using this slide, a predetermined amount of an aqueous sample solution containing a substance to be analyzed (analyte) is placed on the multilayer chemical analysis film of the chemical analysis slide. The slide is maintained at a constant temperature for a predetermined period of time after which it is irradiated with electromagnetic rays of a wavelength determined in accordance with the analyte and the reagent which is contained in the reagent layer of the multilayer chemical analysis film of the slide. Reflection or transmission optical density in a coloration area of the reagent layer is measured to obtain the concentration of the analyte. It should be noted that the transmission optical density measurement is carried out after layers or materials which prevent transmission of measuring rays have been removed.

Specific examples of the multilayer chemical analysis film are multilayer integral-type materials for analysis as described in Japanese Laid-Open Patent Application Nos. 53888/1974 (U.S. Pat. No. 3,992,158), 137192/1975 (U.S. Pat. No. 3,983,005), 40191/1976 (U.S. Pat. No. 4,042,335), 3488/1977 (U.S. Pat. No. Re. 30,267), 131786/1977 (U.S. Pat. No. 4,050,898), 142584/1977 (U.S. Pat. Nos. 4,053,381; 4,136,036; 4,050,451), 33651/1980 and 164356/1980. These multilayer chemical analysis films have a laminate film structure in which a reagent layer or layers and a porous spreading layer are formed integrally on a water-impenetrable support. If a constant amount of liquid as a test sample is dropped onto the outermost layer of the film, the liquid spreads to substantially a constant area and passes through the lower layer whereupon a reaction such as a coloration reaction takes place with the amount of coloration change being in proportion to the concentration of the analyte. By measuring the optical density of the coloration after a predetermined time, the concentration of the analyte in the liquid is colorimetrically determined. In this multilayer chemical analysis film, the outermost layer thereof is covered with a porous film of a type which substantially uniformly spreads the solution under test. Such a material is disclosed, for instance, in Japanese Laid-Open Patent Application No. 164356/1980 and U.S. Pat. No. 3,992,158.

In order to maintain a constant temperature of the multilayer chemical analysis film or the chemical analysis slide having the film, there has conventionally been used a device such as an incubator. Although conventional incubation may be capable of maintaining a constant temperature (37° C. to 40° C., for instance), using this device, the water component in the reagent layer which serves as a solvent or a dispersion medium in aqueous liquid samples tends to evaporate from the multilayer chemical analysis film thereby making it impossible to sufficiently accomplish reaction of the analyte and the reagent. Therefore, there is a tendency for the measured optical density of the coloration to be smaller than an actual optical density thereof. This results in an error in that the concentration of the analyte is erroneously determined, thereby making it impossible to obtain an analysis result with a desirably high accuracy.

In view of this drawback, it has been proposed to provide a cover for sealing the chemical analysis slide so that the multilayer chemical analysis film thereof is isolated from the outer atmosphere during the measurement operation. Using this technique, however, there are drawbacks in that the constitution of the slide, which can be used only once and then must be thrown away, becomes complex thereby increasing the manufacturing cost, rendering the temperature maintaining operation troublesome, and making it difficult to automate the analysis. Furthermore, the analyte can be easily contaminated.

Accordingly, an object of the present invention is to overcome the drawbacks accompanying the prior art devices as mentioned above by providing a device for maintaining a constant temperature during chemical analysis which has a simple construction and which is capable of actively preventing the evaporation of the water component from a multilayer chemical analysis film to which an aqueous liquid sample containing a substance to be measured (analyte) is applied as well as maintaining the quantity of water component and hence the concentration constant during the reaction period. Furthermore, it is desired to provide a device of this type in which the period of time for maintaining the constant temperature can be set as desired.

SUMMARY OF THE INVENTION

In accordance with these and other objects of the invention, there is provided a device for maintaining a constant temperature for chemical analysis including means for conveying at least one slide for chemical analysis with the slide being of a type having at least one layer adapted to absorb a substance to be analyzed (analyte), means for driving the slide conveying means, means for maintaining the slide at a constant temperature, and means for sealing the layer adapted to absorb the analyte in areas where the slide is conveyed at a constant temperature.

In a preferred embodiment, the conveying means is a conveying belt which may be flat, or provided with a plurality of projections for pushing slides, or it may be a belt having recesses formed therein adapted for receiving slides. The sealing means may be a sealing guide belt having a surface disposed opposite the upper surface of the conveying belt with the slides passing between the sealing guide belt and the conveying belt. The sealing guide belt and the conveying belt preferably have an outer surface made of a non-tacky and non-adhesive material such as polytetrafluoroethylene. A guide member may be disposed within the sealing guide belt. Otherwise, the guide member may itself form the sealing means. Still further, the conveying means may be constituted by a disc-shaped conveying member which is rotated while the sealing member is a disc-shaped stationary member disposed above an upper surface of the disc-shaped conveying member.

DESCRIPTION OF THE PREFERRED EMBODIMENTS

Figure 1:
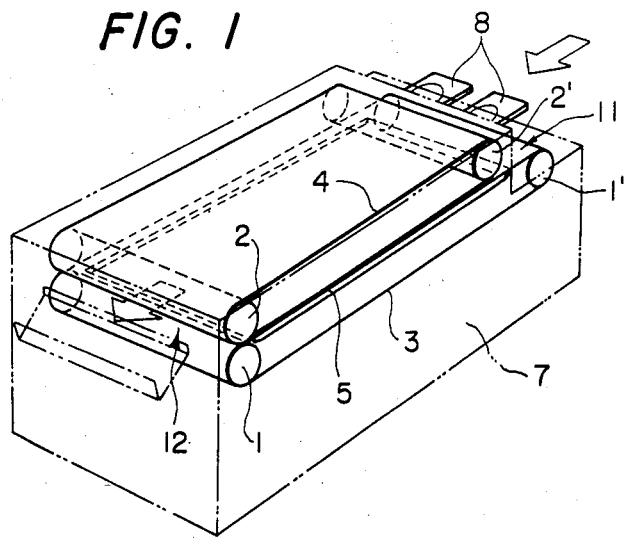
FIG. 1 is a schematic perspective view showing essential parts of a device for maintaining a constant temperature for chemical analysis in accordance with the present invention.

FIG. 1 is a schematic perspective view showing essential parts of a preferred embodiment of a device for maintaining a constant temperature for chemical analysis in accordance with the present invention. In FIG. 1, reference numerals 1 and 1' denote a pair of rollers which are driven by an electric motor (not shown). A conveying belt 3 for conveying a chemical analysis slide 8 having a multilayer chemical analysis film for chemical analysis is laid around the pair of rollers 1 and 1'. The conveying belt 3 is made of a durable material having a high thermal conductivity and which is difficult to deform. Reference numerals 2 and 2' denote a pair of rollers around which is provided a sealing guide belt 4 which acts to seal a multilayer chemical analysis film of the slide 8, into which a substance to be measured (analyte) is absorbed while at the same time acting as a guide for the slide. Reference numeral 5 denotes a member for maintaining a constant temperature which is a metal member having a high thermal conductivity such as aluminum, copper or the like in which an electric element for heating and/or cooling is encased so as to maintain the slide 8 at a constant temperature for a predetermined period of time. As this electric element, for example, a heater or cooling element which makes use of the Peltier effect may be used. Reference numeral 7 denotes a housing in which the above-mentioned components are protectively mounted. In the discussion below, an example will be described in which the electric element is an electric heater.

Figure 2:
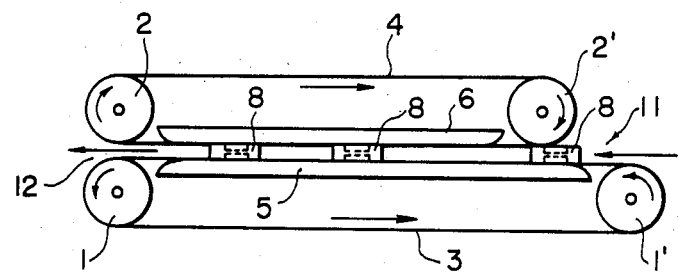
FIG. 2 is a side view showing a first embodiment of conveying and sealing members of the present invention.
Figure 3:
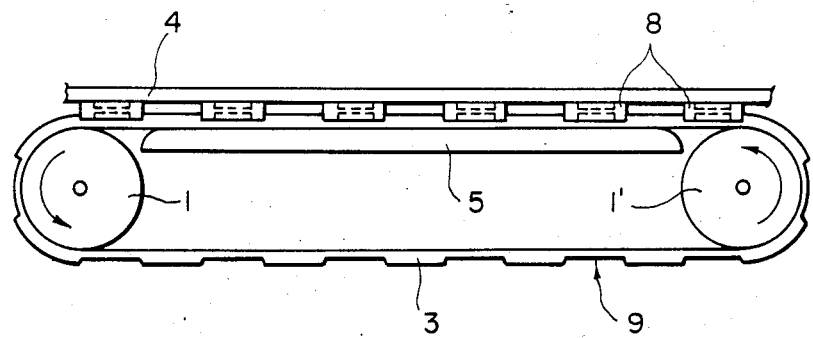
FIG. 3 is a side view showing a second embodiment of conveying members of the present invention.
Figure 4:
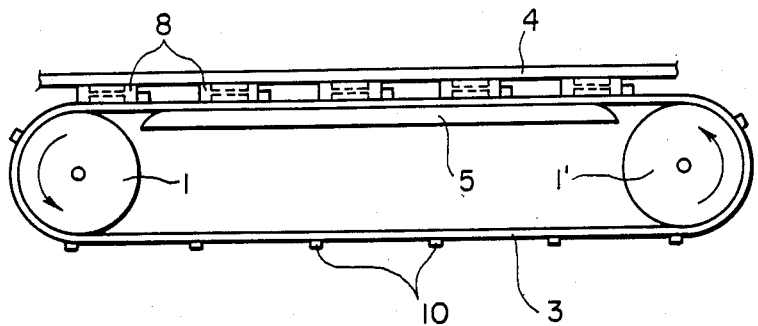
FIG. 4 is a side view showing a third embodiment of conveying members of the present invention.
Figure 6:
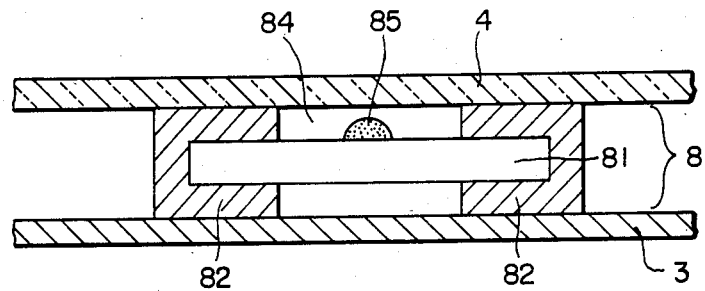
FIG. 6 is an enlarged view of essential components of FIG. 2.

FIG. 2 is a side view of a first embodiment of the conveying and sealing members of the device of FIG. 1. FIG. 6, which is an enlarged view of essential parts of FIG. 2, shows the manner in which the slide 8 is kept at a constant temperature and conveyed while the multilayer chemical analysis film into which the analyte is absorbed is sealed. Reference numeral 81 denotes a multilayer chemical analysis film, reference numeral 82 denotes a slide frame, reference numeral 84 denotes a space and reference numeral 85 denotes an aqueous liquid sample containing an analyte. FIGS. 3 and 4 are side views respectively showing second and third embodiments of the conveying members in accordance with the present invention. In FIG. 3 and FIG. 4, like reference numerals to those employed in FIG. 1 denote like members.

As clearly seen from FIG. 2, a heater 5 is provided in the vicinity of the conveying belt 3. The slide 8 is heated through the conveying belt 3. The sealing guide belt rollers 2 and 2' are rotatably mounted on the casing 7 in such a way that the sealing guide belt 4 which is provided around the rollers 2 and 2' is always in contact with the upper part of the slide 8 as shown so as to seal the slide as the slide is conveyed. As the material for the sealing guide belt, a sheet of polytetrafluoroethylene (PTFE), a sheet of fiber glass or the like impregnated with PTFE or having an outer layer of PTFE, a sheet of silicon rubber or the like may be employed.

As clearly seen from FIG. 6, the film 81 is sealed by the sealing guide belt 4. Specifically, there is formed a tightly closed space 84, on the side of the film 81 where the aqueous liquid sample is provided, by the slide frame 82 and the sealing guide belt 4.

The arrows in the drawings indicate the direction of rotation of the rollers and the belt as well as the conveying direction of the slide 8. In the first embodiment which is shown in FIG. 2, there is provided a guide member 6 used to further enhance the sealing effect between the sealing guide belt 4 and the upper part of the slide 8 as mentioned above. Since both the guide member 6 and the heater 5 are in contact with the sealing guide belt 4 and the conveying belt 3, a surface treatment such as PTFE coating may be applied thereon so as to decrease frictional resistance due to the contact. A heater may be provided in the guide member 6 to perform the heating function not only from above but also from below and thus effecting precise temperature control so as to enhance the heating efficiency.

Although the sealing guide belt as well as the guide member 6 are provided in the above-described first embodiment, it is not necessary to provide both of the sealing guide belt and the guide member 6 if the device is otherwise constructed in such a way as to seal the upper part of the slide 8 so as to prevent evaporation of the water component from the multilayer chemical analysis film 81 during conveying of the slide while a constant temperature is maintained. In case only the guide member 6 is provided which then also performs the sealing function, the frictional resistance between the guide member 6 and the upper part of the slide 8 becomes an important consideration. Specifically, it is desirable to decrease the frictional resistance due to surface contact by providing a PTFE coating or the like. If required, the guide member 6 may be biased towards the slide 8 by any suitable biasing device so as to enhance the sealing effect.

Next, the construction of the second and third embodiments of the conveying members in accordance with the present invention, in particular, the conveying belt 3, will be described with reference to FIG. 3 and FIG. 4.

In the first embodiment shown in FIG. 2, the conveying belt 3 is a conventionally employed conveying belt of a flat type. In the second embodiment shown in FIG. 3, however, the conveying belt 3 is implemented with a belt as shown in the drawing in which a plurality of recesses 9 for receiving the multilayer slides are provided on the surface of the belt. The belt 3 in this embodiment is constructed as a sheet or the like composed of a wire net made of rubber having a high thermal conductivity, polytetrafluoroethylene (PTFE), copper or the like with an outer layer of PTFE, rubber or the like thereon. With this construction, the conveying operation is quite effective.

In the third embodiment shown in FIG. 4, the conveying belt 3 is provided with projections 10 having configurations as shown in the drawing for pushing the slide 8 in the conveying direction instead of the recesses 9 in the second embodiment. The third embodiment provides substantially the same effect as attained in the second embodiment where a multilayer slide having a square shape is conveyed.

In the first, second and third embodiments as described above, the period of time for maintaining a constant temperature of the slide 8 is easily determined in accordance with the required reaction time of the analyte and the reagent by controlling the rotational speed of the electric motor for driving the conveying members. In addition, it is possible to provide a constant period of time during which a constant temperature is maintained.

Figure 5:
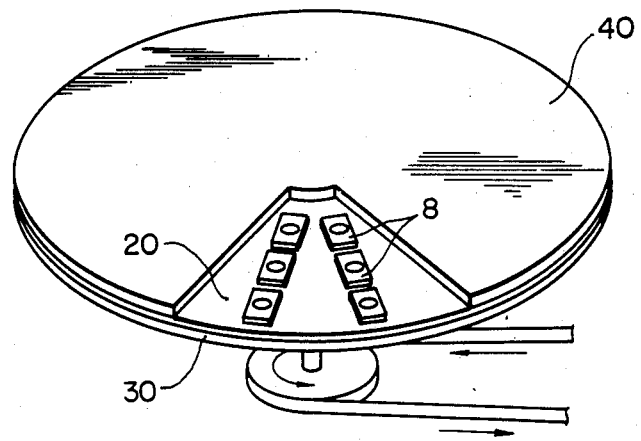
FIG. 5 is a schematic perspective view showing essential parts of another embodiment of a device for maintaining a constant temperature for chemical analysis in accordance with the present invention.

In a still another embodiment of the conveying members, as shown in FIG. 5, a disc-like conveying member 20 is provided which has a plurality of recesses for receiving the slides 8. This conveying member 20 is rotatably and coaxially provided on a disc-like heater 30 and is driven by an electric motor in the same manner as in the above-described embodiments. The period of time for maintaining a constant temperature may be set to a predetermined value as desired by controlling the rotational rate of the electric motor. A sealing member 40 is provided on the disc-like conveying member 20 so as to be in contact with the upper part of the slides 8 and to prevent evaporation of the water component from the multilayer chemical analysis film 81. The sealing member 40 is provided with cut portions for receiving and discharging the slides 8. In this embodiment too, it is desirable that a surface treatment such as a coating of PTFE be provided on the surface of the sealing member 40 which is in contact with the upper surface of the slides 8, taking into consideration the decrease in frictional resistance due to the contact. Furthermore, the sealing member 40 may also be provided with a heater so as to heat the slides 8 from both sides.

As is believed clear from the above explanation, since the multilayer chemical analysis film of the chemical analysis slide is always sealed by a sealing guide belt, a sealing guide member or other sealing member during the constant temperature maintenance operation, evaporation of the water component is actively prevented during the reaction time of the analyte and the reagent. As a result, the quantity of the water component is maintained constant thereby making it possible to carry out the analysis with a high accuracy. In addition, the period of time during which the constant temperature is maintained can also be accurately controlled and simply set by control of the rotational speed of the electric motor for driving the conveying members.

The belt width, the number and configuration of the projections or recesses for receiving the chemical analysis slides, and the material of the belt are not limited to those disclosed in the preferred embodiments described above but may be varied in accordance with a particular application.

What is claimed is:

1. A device for maintaining a constant temperature for chemical analysis, comprising:
   at least one slide having a multi-layer chemical analysis film for receiving an analyte to be measured, said film being supported by a slide frame, said slide frame supporting said film at an intermediate portion thereof so that upper flat surfaces of said slide frame are disposed at an elevation above an upper surface of said film;
   a conveying belt for conveying said slide on a first surface thereof, and a sealing guide belt for sealing said upper flat surfaces of said slide frame so that a first surface of said sealing guide belt which is disposed parallel to said first surface of said conveying belt bridges said upper flat surfaces to form a closed chamber above said upper surface of said film and said analyte to minimize evaporation of said analyte within said closed chamber;
   first and second drive rollers and an electric motor operatively disposed to rotate at least one of said drive rollers to transport said conveying belt; and
   means for maintaining said slide at a constant temperature as said slide is conveyed and sealed.

2. The device of claim 1, further comprising means for maintaining said slide at said constant temperature for a predetermined period of time.

3. The device of claim 1, wherein said conveying belt is provided with a plurality of recesses adapted for receiving a plurality of said multi-layer slides.

4. The device of claim 1, wherein said sealing guide belt comprises a material selected from the group consisting of a sheet of polytetrafluoroethylene, a sheet of fiber glass impregnated with polytetrafluoroethylene, a sheet of fiber glass having an outer layer of polytetrafluoroethylene, and a sheet of silicon rubber.

5. The device of claim 1, wherein said conveying belt comprises a material selected from the group consisting of a wire net coated with rubber, a wire net coated with polytetrafluoroethylene, a sheet of copper having an outer layer of polytetrafluoroethylene, and a copper sheet having an outer layer of rubber.

6. The device of claim 1, further including third and fourth rollers for guiding said sealing guide belt, said conveying belt and said sealing guide belt each comprising endless belts.

7. The device of claim 6, wherein said constant temperature maintaining means comprises a member of a metal having a high thermal conductivity and an electric heating element disposed within said metal member, said metal member being disposed adjacent a back side of said first surface of said endless conveying belt.

8. The device of claim 7, further comprising a guide member disposed between upper and lower runs of said sealing guide belt and being parallel to said metal member and adjacent a back side of said first surface of said sealing guide belt.

9. The device of claim 8, wherein said guide member comprises a heater.

10. The device of claim 8, wherein said conveying belt is provided with a plurality of projections arranged for force-transmitting engagement with a plurality of said multi-layer slides.

11. The device of claim 1, wherein a stationary metal member is disposed opposite said first surface of said conveying belt.

12. The device of claim 11, wherein said stationary member is coated with a layer of polytetrafluoroethylene in regions adjacent said upper sealing surfaces of said slide frame.

13. The device of claim 1, wherein a first outer surface of said sealing guide belt and a first outer surface of said conveying belt are coated with non-tacky and non-adhesive material.

14. The device of claim 13, wherein said non-tacky and non-adhesive material is polytetrafluoroethyrene.

15. A device for maintaining a constant temperature for chemical analysis, comprising:

at least one slide having a multi-layer chemical analysis film for receiving an analyte to be measured, said film being supported by a slide frame, said slide frame supporting said film at an intermediate portion thereof so that upper flat surfaces of said slide frame are disposed at an elevation above an upper surface of said film;

conveying and sealing means including a rotatable disc-shaped conveying member having a plurality of recesses formed therein for receiving a plurality of said multi-layer slides and a disc-shaped sealing member disposed opposite said disc-shaped conveying member, said sealing member having a lower surface in contact with said upper flat surfaces of said slide frames.

16. The device of claim 15, wherein said lower surface of said sealing member is coated with a non-tacky and non-adhesive material.

17. The device of claim 16, wherein said lower surface of said sealing member is coated with polytetrafluoroethylene.

* * * * *